(12) United States Patent
Billingsley

(10) Patent No.: US 6,206,698 B1
(45) Date of Patent: Mar. 27, 2001

(54) PLIABLE COMPOSITE CONDENSING INSTRUMENT

(76) Inventor: Cheryl B. Billingsley, 2423 Old Coach La., Richmond, VA (US) 23233

(*) Notice: Subject to any disclaimer, the term of this patent is extended or adjusted under 35 U.S.C. 154(b) by 0 days.

(21) Appl. No.: 09/452,613

(22) Filed: Dec. 1, 1999

(51) Int. Cl.$^7$ ........................................ A61C 3/08
(52) U.S. Cl. ............................................. 433/164
(58) Field of Search ................... 433/164, 147, 433/83

(56) References Cited

U.S. PATENT DOCUMENTS

| | | | |
|---|---|---|---|
| 532,721 | * | 1/1895 | Dennis ................................. 433/164 |
| 4,521,191 | * | 6/1985 | Ehrnford .............................. 433/164 |
| 4,586,901 | * | 5/1986 | Tanaka et al. ....................... 433/164 |
| 5,358,404 | * | 10/1994 | Schumacher ......................... 433/164 |

* cited by examiner

Primary Examiner—John J. Wilson
Assistant Examiner—Melba Bumgarner
(74) Attorney, Agent, or Firm—Greenblum & Bernstein P.L.C.

(57) ABSTRACT

A hand-held dental instrument for use in condensing and packing soft, composite filling material. The condenser includes resiliently pliable, bulbous tips of various diameters, having a pliable surface such as rubber or soft plastic that deforms under hand pressure and returns to its original shape upon removal of said pressure. The condenser enables a dentist, dental assistant or technician to condense efficiently and uniformly composite filling material into a prepared tooth cavity. The condenser is an improvement over the typical existing art, which comprises rigid metal, plastic or ceramic tips of relatively small diameter, designed for condensing silver amalgam filling material. The condensing instrument provides a solution to the problem of rigid tipped condensing instruments applying uneven pressure into the soft composite, pushing holes or air pockets into the material rather than condensing it.

6 Claims, 1 Drawing Sheet

PLIABLE COMPOSITE CONDENSING INSTRUMENT

BACKGROUND OF THE INVENTION

The present invention relates to a hand-held dental tool used to condense, or pack, soft composite filling into a prepared tooth cavity. The tool comprises an elongated handle, not unlike dental tool handles common to the industry, with at least one end angled in a manner to permit easy and efficient access to a patient's tooth surfaces. Attached to each angled end of the elongated handle is a bulbous, malleable head of sufficient diameter to cover the average human tooth.

The existing art dental instruments commonly used to condense filling material have rigid metal, plastic or ceramic tips, which were designed to accommodate condensing silver amalgam alloys into tooth cavities. The rigid tips are not conducive to compressing soft composite filling in that they displace the soft filling material without condensing it, apply uneven compression, generally, and potentially causing holes and air pockets to form in the material. The result is that dental professionals waste time and often resort to use of fingers to achieve uniform pressure over the composite surface sufficient to condense the material evenly into the prepared cavity.

OBJECTS AND SUMMARY OF THE INVENTION

It is an object of the invention disclosed herein to provide a relatively low cost dental instrument that can be used to condense soft, composite filling material into a prepared tooth cavity, uniformly and efficiently, reducing or eliminating problems associated with uneven compression, including inducing holes and air pockets into the filling material.

It is another object of the invention disclosed herein to achieve application of uniform pressure across the surface of composite filling material through deformation of a bulbous, malleable tip in response to physical force applied by the dental professional.

It is another object of the invention disclosed herein to maximize efficiency in condensing soft, composite filing material and to minimize chair-time of the patient.

The invention achieves the above objects by providing a simply-designed, handheld dental instrument having an elongated handle with at least one angled end, to which is attached a bulbous, pliable tip. The tip would be available in various sizes to accommodate anticipated variations in human tooth sizes. The dental professional would prepare a tooth cavity for filling in the traditional manner through drilling and insert soft, composite filling material into the prepared cavity. The filling material would then be condensed using the disclosed invention by insertion of the instrument into the patient's mouth, placement of the pliable tip onto the exposed surface area of the composite filling material and application of pressure in the direction of the filling material sufficient to compress the material into the prepared cavity. The application of pressure would be repeated until desired compression is achieved.

BRIEF DESCRIPTION OF THE DRAWINGS

The invention is illustrated in the figures of the accompanying drawings are meant to be exemplary and not limiting.

DETAILED DESCRIPTION OF THE INVENTION

The present invention is directed at providing an inexpensive and simply designed instrument for condensing soft dental composite materials inside a tooth cavity under uniform pressure. It will prevent inefficient and time-consuming use of rigid-tipped dental tools that, although having a similar purpose, were not designed for use with soft filling material.

U.S. Pat. No. 4,521,191 to Ehrnford entitled, "Condensing instrument for packing and condensing in connection with placement of dental composite resin restorative materials" discloses an example of the existing art of dental condensing tools having rigid tips. Although the patent discusses use of the invention with composite filling materials, as opposed to traditional silver amalgam alloys, it still discloses a hard surfaced condenser. In particular, the invention discloses only rigid surfaces of sufficient integrity, such as glass or porcelain ceramic coatings and cobalt and chromium alloys, so as to prevent scratching and discoloration of the instrument itself. Nowhere does the invention address or even contemplate a yieldable head or tip that conforms to the surface and applies uniform pressure to the soft, composite filling.

U.S. Pat. No. 4,586,901 to Tanaka, et al., entitled, "Method and instrument for condensing restorative dental materials" discloses a hand-held instrument for condensing soft, composite materials having an elastomeric tip, which invention is similar to the subject invention only to the extent both contemplate pliable as opposed to rigid tips. Otherwise, the invention disclosed herein is superior to this prior art in that it has a simpler, more efficient design that is easier to use and probably less expensive to produce. In particular, the Tanaka invention very specifically discloses and claims only a contoured tip, having "raised peripheral regions" and a "raised central region," such that the tip would generally define and conform to the shape of a tooth, distally. Tanaka's drawings further reveal the intricate nature of the elastomeric tips disclosed in the invention, all of which show cup-like peripheral walls surrounding an interior protrusion. There is no embodiment described or claimed in the Tanaka's specification that does not have the peripheral walls in combination with the raised interior. There also is no embodiment described or claimed comprising a simple, bulbous, pliable tip with no predetermined contour, but which accomplishes the purpose of applying uniform pressure across the exposed surface of the soft composite filling solely through disfiguration of the bulbous tip in response to physical force applied by the dental professional. In other words, the subject invention conforms to the shape of the tooth only to the extent sufficient force is applied.

Figure 1:
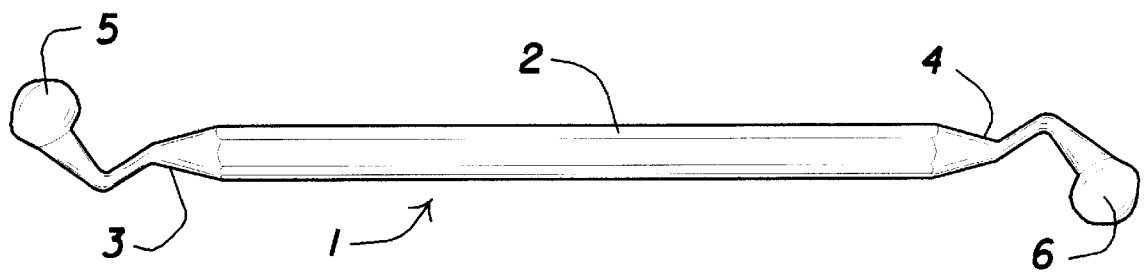
FIG. 1 is a side view of one illustrative embodiment of the composite condensing instrument comprising an elongated handle with angled ends, to each of which is attached bulbous, pliable tips.

Referring to the drawings described above, the composite condensing instrument 1 in FIG. 1 of the present invention comprises an elongated handle 2 with at least one end bent at an angle to accommodate efficient access to the interior of a patient's mouth. The preferred embodiment contains bent portions of the handle 3 and 4 on both ends. On each bent end is attached a pliable bulbous tip 5 and 6 of FIG. 1 and 7 of FIG. 2. Each tip would be of a size and diameter generally compatible with the distal surface of average-sized human molars, the preferred embodiment being 6.35 to 19.05 millimeters (0.25 to 0.75 inch) in diameter, although the invention contemplates any dimensions suitable for use in a human mouth. The preferred embodiment includes different sizes of bulbous tips on each end of a single handle, either securely fastened or removable. It is anticipated that the invention would be made available to the public in sets, consisting of handles with bulbous tips ranging in size incrementally from small to large.

The invention would be autoclavable to accommodate sterilization. An autoclave is a means of sterilizing dental equipment generally, comprising the exposure of items to steam heat of at least 100 degrees centigrade (212 degrees Fahrenheit) for a minimum of 3 minutes at high pressure or 45 minutes at ambient pressure. Autoclavability is critical to the purpose of the invention, as it is to be used directly in the treatment of patients.

Figure 2:
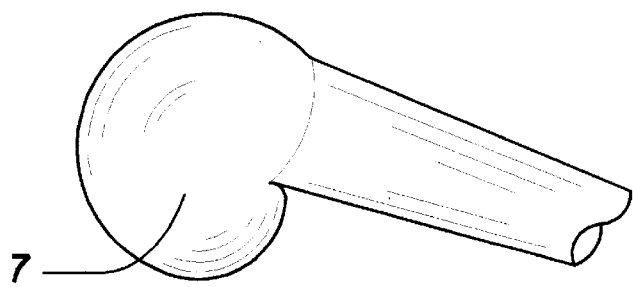
FIG. 2 is a perspective view of the bulbous tip, showing the general shape of the invention.
Figure 3:
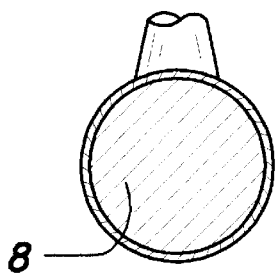
FIG. 3 is a cross-sectional view from the bottom of the instrument, taken along the diameter of the tip showing solid, pliable core and surface material.
Figure 4:
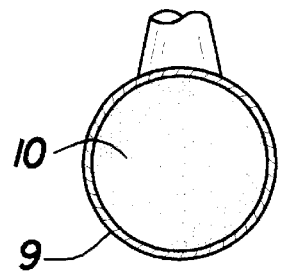
FIG. 4 is a cross-sectional view from the bottom of the instrument, taken along the diameter of the tip showing granular core material and pliable surface material.

The bulbous tips 5 and 6 in FIG. 1 and 7 in FIG. 2 are sufficiently pliable to deform when pressed against a rigid surface, expanding the contact surface area between the pliable tip and rigid surface. The preferred embodiment would deform and expand to effectively cover the distal surface of an average-sized human molar. The tip would also be sufficiently resilient so as to return to its original shape and dimensions upon the removal of external force against the rigid surface. The tip can be made of any material exhibiting these mechanical characteristics. The preferred embodiment consists of solid, yet appropriately pliable, rubber or elastomer material 8 in FIG. 3 throughout the tip. An alternative embodiment comprises a tip with a pliable rubber or elastomer surface material 9 of FIG. 4 containing a granular core material 10 of FIG. 4. The core material must be granular silicon or like substance ground into sufficiently fine particles so as to avoid uneven protrusions through the pliable surface material 9. As in the preferred embodiment, the combination surface material and filler tip of FIG. 4 will be sufficiently resilient so as to return to its original, generally bulbous shape and dimensions upon the removal of exterior force pressing it against the tooth. Again, all materials should be autoclavable so that the entire instrument may be sterilized as appropriate.

Having now described the invention in detail in accordance with the requirements of the patent statutes, those skilled in this art will have no difficulty in making changes and modifications in the individual parts or their relative assembly in order to meet specific requirements or conditions. Such changes and modifications may be made without departing from the scope and spirit of this invention, as set forth in the following claims.

What is claimed is:

1. A dental instrument for condensing soft composite filling material, comprising a rigid, elongated handle having two ends, at least one of said two ends being bent at an angle; and a bulbous, resiliently pliable tip attached to each bent end of said handle, wherein said bulbous, resiliently pliable tip comprises a sheet of pliable surface material covering and encasing granular filler material.

2. The dental instrument for condensing soft composite filling material according to claim 1 wherein said sheet of pliable surface material comprises a pliable rubber surface material.

3. The dental instrument for condensing soft composite filling material according to claim 1 wherein said sheet of pliable surface material comprises a pliable elastomer surface material.

4. A dental instrument for condensing soft composite filling material, comprising a bulbous, resiliently pliable tip, said tip comprising a sheet of pliable surface material covering and encasing granular filler material and having an original shape and dimensions; and a rigid, elongated handle to which said tip is attached;

wherein said tip is sufficiently rigid to condense composite filling material into a prepared cavity in a tooth upon application of an external physical force directed toward the surface of the tooth; sufficiently pliable to deform under the external physical forces such that the area of mutual contact between the deformed tip and the tooth is approximately the size of the distal surface of an average human molar; and sufficiently resilient to return to its original shape and dimensions upon removal of the external physical force.

5. The dental instrument for condensing soft composite filling material according to claim 4 wherein said sheet of pliable surface material comprises a pliable rubber surface material.

6. The dental instrument for condensing soft composite filling material according to claim 4 wherein said sheet of pliable surface material comprises a pliable elastomer surface material.

* * * * *